United States Patent
Mashima et al.

(10) Patent No.: US 8,431,709 B2
(45) Date of Patent: Apr. 30, 2013

(54) ACYLATION REACTION OF HYDROXYL GROUP

(75) Inventors: Kazushi Mashima, Osaka (JP); Takashi Ohshima, Osaka (JP); Takanori Iwasaki, Osaka (JP); Noboru Sayo, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 442 days.

(21) Appl. No.: 12/682,591

(22) PCT Filed: Oct. 10, 2008

(86) PCT No.: PCT/JP2008/002864
§ 371 (c)(1),
(2), (4) Date: Apr. 9, 2010

(87) PCT Pub. No.: WO2009/047905
PCT Pub. Date: Apr. 16, 2009

(65) Prior Publication Data
US 2010/0249422 A1    Sep. 30, 2010

(30) Foreign Application Priority Data
Oct. 11, 2007    (JP) .................................. 2007-265946

(51) Int. Cl.
*C07D 211/34*    (2006.01)
*C07D 207/08*    (2006.01)
*C07C 69/78*    (2006.01)

(52) U.S. Cl.
USPC ............ 546/238; 548/572; 560/106; 560/110

(58) Field of Classification Search ......................... None
See application file for complete search history.

(56) References Cited

U.S. PATENT DOCUMENTS

2009/0198070 A1    8/2009    Mashima et al.

FOREIGN PATENT DOCUMENTS

| JP | 5-148198 A | 6/1993 |
|---|---|---|
| JP | 5-310654 A | 11/1993 |
| WO | 2007/066617 A1 | 6/2007 |

OTHER PUBLICATIONS

XP-002623913—Database WPI Week 199138; Thomson Scientific, London, GB; AN 1991-276726—Abstract—(Aug. 7, 1991).
XP-002623912—Database WPI Week 199009—Thomson Scientific, London, GB; AN 1990-063685—Abstract—(Jan. 22, 1990).
T. Mino et al., "N, O-ligand accelerated zinc-catalyzed transesterification of alcohols with vinyl esters", Journal of Organometallic Chemistry, 692(20), pp. 4389-4396 (2007).
Y. Shirae et al., "Transesterification of various alcohols with vinyl acetate under mild conditions catalyzed by diethylzinc using N-substituted diethanolamine as a ligand", Tetrahedron Letters, Elsevier, Amsterdam, NL, 46(35), pp. 5877-5879 (2005).
T. Ohshima et al., "Direct conversion of esters, lactones, and carboxylic acids to oxazolines catalyzed by a tetranuclear zinc cluster", Chemical Communications, pp. 2711-2713 (2006).

*Primary Examiner* — Janet Andres
*Assistant Examiner* — Timothy R Rozof
(74) *Attorney, Agent, or Firm* — Edwards Wildman Palmer LLP; Peter F. Corless; Christine C. O'Day

(57) ABSTRACT

Disclosed is a selective ester production process of an alcoholic hydroxyl group, which proceeds under chemically mild conditions, while having adequate environmental suitability, operability and economical efficiency. Specifically disclosed is a process for producing an ester compound, which is characterized in that an alcohol and a carboxylic acid ester compound are reacted in the presence of a compound containing zinc element, thereby selectively acylating a hydroxyl group of the alcohol.

2 Claims, No Drawings

ACYLATION REACTION OF HYDROXYL GROUP

CROSS-REFERENCES TO RELATED APPLICATIONS

This application is a U.S. national phase application, pursuant to 35 U.S.C. §371 of PCT/JP2008/002864, filed Oct. 10, 2008, designating the United States, which claims priority to Japanese Application No. 2007-265946, filed Oct. 11, 2007. The entire contents of the aforementioned patent applications are incorporated herein by this reference.

TECHNICAL FIELD

The present invention provides a process for producing an ester compound by performing a transesterification reaction in the presence of a catalyst containing zinc element.

BACKGROUND ART

Ester compounds are abundantly found in nature, as well as in medicines, agrochemicals, perfumes, functional materials and the like. In the syntheses of these materials, reactions between corresponding alcohols and carboxylic acids, carboxylic acid chlorides, carboxylic acid anhydrides and the like, or trans-esterification reactions making use of ester compounds are widely used. A series of methods play an important role not only for the purpose of producing ester compounds, but also as a method for protecting a hydroxyl group or a carboxyl group.

A method of using an ester compound derived from a low boiling point alcohol as an acylating agent (transesterification reaction) can be said to be a technique excellent in operability and economic efficiency from the aspect that obtainment (preparation) and handling of the acylating agent are easy, and also that separation of the target product can be carried out in a short step. There have been developed, as the transesterification reaction, classical methods of using a protic acid, as well as many methods of using an aluminum compound, a tin compound or the like as a catalyst. However, these catalysts frequently catalyze not only the intended transesterification reaction, but also undesirable side reactions. Furthermore, when tin compounds are used as catalysts, problems are posed by waste disposal of harmful tin compounds, tin compounds remaining in the products, and the like. An example of the undesirable side reactions may be a decomposition reaction of a functional group that is labile to acid, for example, an alkylideneacetal, a tetrahydropyranyloxy group, a silyloxy group or the like, which are commonly used as protective groups. In addition, racemization which readily undergoes under acidic or basic conditions in the case where there is co-present an asymmetric center, and polymerization reactions in the case where an unsaturated aliphatic group is included, are also included in the undesirable side reactions.

Performing acylation of alcohols each having plural nucleophilic functional groups, as represented by aminoalcohols, in a hydroxyl group-selective manner, is also an important task. A main factor for the occurrence of chemical selectivity in the transesterification reaction may be mentioned as the dependency on the activity of used catalysts, the difference in nucleophilicity of various functional groups, and the stability of produced acyl compounds. For example, Non-Patent Document 1 describes an acylation reaction of aminoalcohols using an aluminum compound as a catalyst, but amide forms in which the amino group is acylated, are obtained as the main resultant product. Furthermore, Non-Patent Document 2 describes an acylation reaction of aminoalcohols in the presence of a carbene catalyst, but amide forms are mainly produced as in the case described above.

Non-Patent Document 1: The Journal of Organic Chemistry 1988, 53, 4172.

Non-Patent Document 2: Organic Letters 2005, 7, 2453.

DISCLOSURE OF THE INVENTION

Problems to be Solved by the Invention

That is to say, in order to obtain an acylated form (ester form) of a hydroxyl group, multiple processes are required for protecting a competing nucleophilic functional group in advance, and then performing esterification and deprotection, and therefore, this cannot be said to be a production method with high economic efficiency. Under such circumstances, development of an ester production process which combines sustainabillity, operability and economic efficiency and has compatibility for a wide variety of functional groups, is desired.

Means for Solving the Problems

The inventors of the present invention devotedly conducted an investigation on the problems discussed above, and as a result, the inventors found that a transesterification reaction using a carboxylic acid ester compound as an acylating agent in the presence of a zinc compound, is an excellent technique for the production of a wide variety of ester compounds.

That is, the present invention relates to [1] to [4] in the following:

[1] a process for producing an ester compound, the process including allowing a carboxylic acid ester compound to react in a reaction system in which an amino group and an alcoholic hydroxyl group are co-present, in the presence of a compound containing zinc element, and thereby selectively acylating the alcoholic hydroxyl group;

[2] a process for producing an ester compound according to [1], wherein an aminoalcohol is reacted with a carboxylic acid ester compound in the presence of a compound containing zinc element, and thereby a hydroxyl group of the aminoalcohol is selectively acylated;

[3] a process for producing an ester compound according to [1], wherein a mixture of an alcohol and an amine is reacted with a carboxylic acid ester in the presence of a compound containing zinc element, and thereby a hydroxyl group of the alcohol is selectively acylated; and

[4] a process for producing an ester compound according to any one of [1] to [3], wherein the compound containing zinc element is a compound represented by formula (1):

$$Zn_a(OCOR^1)_b Z_c \qquad (1)$$

wherein R' represents an alkyl group which may be substituted, an aryl group which may be substituted, or a heterocyclic group which may be substituted; Z represents an oxygen atom, a sulfur atom or a selenium atom; a represents 1 or 4, b represents 2 or 6, and c represents 0 or 1, provided that when a=1, b=2 and c=0, and when a=4, b=6 and c=1.

Effects of the Invention

According to the production process of the present invention, an alcoholic hydroxyl group in an aminoalcohol can be selectively acylated. An ester compound can also be produced using a mixture of an amine and an alcohol by selectively acylating a hydroxyl group of the alcohol. Furthermore, an ester compound can be efficiently produced also by using a substrate which concurrently has labile functional groups to acid, base or heat.

BEST MODES FOR CARRYING OUT THE INVENTION

Hereinafter, the present invention will be described in detail.

The reaction system having both an amino group and an alcoholic hydroxyl group according to the present invention means that a molecule having an amino group and a molecule having an alcoholic hydroxyl group are simultaneously present in a reaction system, and the molecule having an amino group and the molecule having an alcoholic hydroxyl group may be a same molecule, or may be different molecules. An instance in which the molecule having an amino group and the molecule having an alcoholic hydroxyl group are a same molecule, may be found in aminoalcohols. An instance in which the molecule having an amino group and the molecule having an alcoholic hydroxyl group are different molecules, may be found in a situation where an amine and an alcohol are simultaneously present in a reaction system.

The amino group according to the present invention is preferably a primary amino group or a secondary amino group. The alcoholic hydroxyl group may be any of a primary hydroxyl group, a secondary hydroxyl group and a tertiary hydroxyl group.

The aminoalcohols used in the present invention are not particularly limited as long as they are compounds each having an amino group and an alcoholic hydroxyl group, and examples thereof include linear or branched, cyclic or fused-cyclic, aliphatic or aromatic aminoalcohols, and the like.

An example of the aminoalcohols used in the present invention may be a compound represented by formula (2).

[Chemical Formula 1]

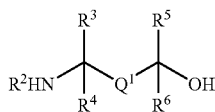

(2)

In the formula (2), $R^2$ represents a hydrogen atom, a hydrocarbon group which may be substituted, or an alkoxycarbonyl group which may be substituted; $R^3$, $R^4$, $R^5$ and $R^6$, which may be identical or different, each represent a hydrogen atom, a hydrocarbon group which may be substituted, an alkoxy group which may be substituted, or a heterocyclic group which may be substituted, or any two groups selected from $R^2$, $R^3$, $R^4$, $R^5$ and $R^6$ may be joined to form a ring; and $Q^1$ represents a linking group.

In the compound represented by the formula (2), the hydrocarbon group represented by $R^2$, $R^3$, $R^4$, $R^5$ or $R^6$ is not particularly limited, but examples include an alkyl group, a cycloalkyl group, an alkenyl group, an alkynyl group, an aryl group, and the like.

The alkyl group may be a linear or branched alkyl group. This alkyl is preferably, for example, an alkyl group having 1 to 20 carbon atoms, preferably 1 to 10 carbon atoms, and more preferably 1 to 6 carbon atoms. This alkyl group is not particularly limited, but may be a linear or branched alkyl group such as a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group, or a stearyl group.

The cycloalkyl group may be, for example, a cycloalkyl group having 3 to 20 carbon atoms, preferably 3 to 10 carbon atoms, and more preferably 3 to 8 carbon atoms. This cycloalkyl group is not particularly limited, but examples include cycloalkyl groups such as a cyclopropyl group, a cyclobutyl group, a cyclopentyl group, a methylcyclopentyl group, a cyclohexyl group, a methylcyclohexyl group and a cyclooctyl group.

The alkenyl group is not particularly limited, but may be a linear or branched alkenyl group having 2 to 20 carbon atoms, preferably 2 to 10 carbon atoms, and more preferably 2 to 6 carbon atoms. Specific examples of the alkenyl group include an ethenyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 1-cyclohexenyl group, a 3-cyclohexenyl group, and the like.

The alkynyl group is not particularly limited, but may be an alkynyl group having 2 to 20 carbon atoms, preferably 2 to 10 carbon atoms, and more preferably 2 to 6 carbon atoms, which may be linear or branched. Specific examples thereof include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, and a 5-hexynyl group, and the like.

The aryl group is not particularly limited, but may be, for example, a monocyclic, polycyclic or fused-cyclic aryl group having 6 to 20 carbon atoms. Specific examples thereof include a phenyl group, a naphthyl group, an anthryl group, a phenanthryl group, a biphenyl group, a terphenyl group, and the like.

The substituents which may be carried by these hydrocarbon groups are not particularly limited as long as they do not exert adverse effects on the acylation reaction of the present invention. Preferred examples of the substituents include a hydrocarbon group, a heterocyclic group, an alkoxy group, an alkylenedioxy group, an aryloxy group, an aralkyloxy group, a heteroaryloxy group, an alkylthio group, an arylthio group, an aralkylthio group, a heteroarylthio group, a hydroxyl group, a nitro group, a trisubstituted silyloxy group, a halogen atom, and the like.

Examples of the hydrocarbon group as a substituent of the hydrocarbon groups include an alkyl group, a cycloalkyl group, an alkenyl group, an alkynyl group, an aryl group, an aralkyl group, and the like.

The alkyl group as a substituent of the hydrocarbon groups may be a linear or branched alkyl group, and an alkyl group having 1 to 20 carbon atoms is preferred. Examples thereof include a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group, a stearyl group, and the like.

The cycloalkyl group as a substituent of the hydrocarbon groups may be a cycloalkyl group having 3 to 10 carbon atoms, and examples thereof include cycloalkyl groups such as a cyclopropyl group, a cyclobutyl group, a cyclopentyl group, a cyclohexyl group, and a cyclooctyl group, and the like.

The alkenyl group as a substituent of the hydrocarbon groups may be linear or branched, and may be, for example, an alkenyl group having 2 to 15 carbon atoms, preferably 2 to 10 carbon atoms, and more preferably 2 to 6 carbon atoms. Specific examples thereof include a vinyl group, a 1-propenyl group, an allyl group, a 1-butenyl group, a pentenyl group, a hexenyl group, and the like.

The alkynyl group as a substituent of the hydrocarbon groups may be linear or branched, and may be, for example, an alkynyl group having 2 to 15 carbon atoms, preferably 2 to 10 carbon atoms, and more preferably 2 to 6 carbon atoms. Specific examples thereof include an ethynyl group, a 1-propynyl group, a 2-propynyl group, a 1-butynyl group, a 3-butynyl group, a pentynyl group, a hexynyl group, and the like.

The aryl group as a substituent of the hydrocarbon groups may be, for example, a monocyclic, polycyclic or fused-cyclic aryl group having 6 to 20 carbon atoms, and specific examples thereof include a phenyl group, a naphthyl group, an anthryl group, a phenanthryl group, a biphenyl group, a terphenyl group, and the like.

The aralkyl group as a substituent of the hydrocarbon groups may be a group resulting from substitution of at least one hydrogen atom of an alkyl group such as mentioned above, with an aryl group such as mentioned above, and for example, an aralkyl group having 7 to 12 carbon atoms is preferred. Specific examples thereof include a benzyl group, a 2-phenylethyl group, a 1-phenylpropyl group, a 3-naphthylpropyl group, and the like.

The heterocyclic group as a substituent of the hydrocarbon groups may be an aliphatic heterocyclic group or an aromatic heterocyclic group. The aliphatic heterocyclic group may be, for example, a 5- to 8-membered, preferably 5- or 6-membered, monocyclic saturated or unsaturated aliphatic heterocyclic group having 2 to 14 carbon atoms, which contains, as heteroatoms, at least one, preferably 1 to 3, heteroatoms such as a nitrogen atom, an oxygen atom and a sulfur atom; or a polycyclic or fused-cyclic, saturated or unsaturated aliphatic heterocyclic group. Specific examples of the aliphatic heterocyclic group include a piperidino group, a piperazinyl group, a morpholino group, a tetrahydrofuryl group, a tetrahydropyranyl group, a tetrahydrothienyl group, and the like.

The aromatic heterocyclic group as a substituent of the hydrocarbon groups may be, for example, a 5- to 8-membered, preferably 5- or 6-membered, monocyclic heteroaryl group having 2 to 15 carbon atoms, which contains, as heteroatoms, at least one, preferably 1 to 3, heteroatoms such as a nitrogen atom, an oxygen atom and a sulfur atom; or a polycyclic or fused-cyclic heteroaryl group. Specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, an quinolyl group, an isoquinolyl group, a quinoxalyl group, a phthalazinyl group, a quinazolinyl group, a naphthyridinyl group, a cinnolinyl group, a benzimidazolyl group, a benzoxazolyl group, a benzothiazolyl group, and the like.

The alkoxy group as a substituent of the hydrocarbon groups may be, for example, an alkoxy group having 1 to 6 carbon atoms, which may be linear, branched or cyclic. Specific examples thereof include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a cyclohexyloxy group, a methoxymethoxy group, a 2-ethoxyethoxy group, a 2-methoxyethoxymethoxy group, and the like.

The alkylenedioxy group as a substituent of the hydrocarbon groups may be, for example, an alkylenedioxy group having 1 to 3 carbon atoms, and specific examples thereof include a methylenedioxy group, an ethylenedioxy group, a trimethylenedioxy group, a propylenedioxy group, an isopropylidenedioxy group, a benzylidenedioxy group, and the like.

The aryloxy group as a substituent of the hydrocarbon groups may be, for example, an aryloxy group having 6 to 14 carbon atoms, and specific examples thereof include a phenoxy group, a tolyloxy group, a xylyloxy group, a naphthoxy group, an anthryloxy group, and the like.

The aralkyloxy group as a substituent of the hydrocarbon groups may be, for example, an aralkyloxy group having 7 to 12 carbon atoms, and specific examples thereof include a benzyloxy group, a 4-methoxyphenylmethoxy group, a 1-phenylethoxy group, a 2-phenylethoxy group, a 1-phenylpropoxy group, a 2-phenylpropoxy group, a 3-phenylpropoxy group, a 1-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, a 6-phenylhexyloxy group, and the like.

The heteroaryloxy group as a substituent of the hydrocarbon groups may be, for example, a heteroaryloxy group having 2 to 14 carbon atoms, which contains, as heteroatoms, at least one, preferably 1 to 3, heteroatoms such as a nitrogen atom, an oxygen atom and a sulfur atom. Specific examples thereof include a 2-pyridyloxy group, a 2-pyrazyloxy group, a 2-pyrimidyloxy group, a 2-quinolyloxy group, and the like.

The alkylthio group as a substituent of the hydrocarbon groups may be, for example, an alkylthio group having 1 to 6 carbon atoms, which may be linear, branched or cyclic. Specific examples thereof include a methylthio group, an ethylthio group, an n-propylthio group, an isopropylthio group, an n-butylthio group, a 2-butylthio group, an isobutylthio group, a tert-butylthio group, a pentylthio group, a hexylthio group, a cyclohexylthio group, and the like.

The arylthio group as a substituent of the hydrocarbon groups may be, for example, an arylthio group having 6 to 14 carbon atoms, and specific examples thereof include a phenylthio group, a tolylthio group, a xylylthio group, a naphthylthio group, and the like.

The aralkylthio group as a substituent of the hydrocarbon groups may be, for example, an aralkylthio group having 7 to 12 carbon atoms, and specific examples thereof include a benzylthio group, a 2-phenethylthio group, and the like.

The heteroarylthio group as a substituent of the hydrocarbon groups may be, for example, a heteroarylthio group having 2 to 14 carbon atoms, which contains, as heteroatoms, at least one, preferably 1 to 3, heteroatoms such as a nitrogen atom, an oxygen atom and a sulfur atom. Specific examples thereof include a 4-pyridylthio group, a 2-benzimidazolylthio group, a 2-benzoxazolylthio group, a 2-benzothiazolylthio group, and the like.

The trisubstituted silyloxy group as a substituent of the hydrocarbon group may be, for example, a trimethylsilyloxy group, a triethylsilyloxy group, a triisopropylsilyloxy group, a tert-butyldimethylsilyloxy group, a tert-butyldiphenylsilyloxy group, a triphenylsilyloxy group, and the like.

The halogen atom as a substituent of the hydrocarbon group may be a fluorine atom, a chlorine atom, a bromine atom, or an iodine atom. An alkyl group substituted with halogen atoms is an alkyl group such as mentioned above, substituted with halogen atoms, and examples include a monofluoromethyl group, a difluoromethyl group, a trifluoromethyl group, a pentafluoroethyl group, and the like.

The heterocyclic group represented by $R^3$, $R^4$, $R^5$ and $R^6$ may be an aliphatic heterocyclic group or an aromatic heterocyclic group, and specific examples thereof include the same groups as the above mentioned heterocyclic groups as substituents of the hydrocarbon groups. Furthermore, substituents which may be carried by these heterocyclic groups include an alkyl group, an aryl group, a heterocyclic group, and the like, and specific examples of the respective substituents may be the same groups as those mentioned above.

The alkoxy group represented by $R^3$, $R^4$, $R^5$ and $R^6$ may be, for example, an alkoxy group having 1 to 20 carbon atoms, and preferably 1 to 10 carbon atoms, which may be linear, branched or cyclic. Specific examples thereof include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a heptyloxy group, an octyloxy group, a nonyloxy group, a decyloxy group, a cyclohexyloxy group, a methoxymethoxy group, a benzyloxy group, and the like. Substituents which may be carried by the alkoxy group include an alkyl group, an aryl group, a halogen atom, a heterocyclic group, an alkoxy group, and the like. Specific examples of the respective substituents may be groups such as those described previously as the respective substituents of the hydrocarbon groups.

The linking group represented by $Q^1$ in the formula (2) may be a single bond, a divalent hydrocarbon group, an oxygen atom, or the like.

Examples of the divalent hydrocarbon group for $Q^1$ include an alkylene group, an arylene group, and a heteroarylene group.

The alkylene group may be, for example, an alkylene group having 1 to 30 carbon atoms, and preferably 1 to 20 carbon atoms. Specific examples of the alkylene group include a methylene group, an ethylene group, a trimethylene group, a tetramethylene group, a pentamethylene group, a hexamethylene group, a heptamethylene group, an octamethylene group, a nonamethylene group, a decamethylene group, a tetradecamethylene group, a hexadecamethylene group, and the like. These alkylene groups may be substituted with substituents, and examples of the substituents include an alkyl group, an alkoxy group, an aryl group, an alkylenedioxy group, a halogen atom, and the like, such as those mentioned above. Furthermore, at least one carbon atom in the alkylene group may be converted to a divalent group such as an arylene group, a heteroarylene group or an oxygen atom. For example, the alkylene group may contain a phenylene group, a naphthalenediyl group, a pyridinediyl group or the like and form a xylylene group, a —CH$_2$—Np—CH$_2$— group (Np represents a naphthalenediyl group), a —CH$_2$-Py-CH$_2$— group (Py represents a pyridinediyl group) or the like, or may contain an oxygen atom and form an oxaalkylene group having an ether bond.

The arylene group may be, for example, a monocyclic, polycyclic or fused-cyclic arylene group having 6 to 30 carbon atoms, and preferably 6 to 20 carbon atoms. Specific examples of the arylene group include a phenylene group, a naphthalenediyl group, a phenanthrenediyl group, an anthracenediyl group, and the like. These arylene groups may be substituted with substituents, and the substituents include an alkyl group, an alkoxy group, an alkylenedioxy group, a halogen atom and the like, such as those mentioned above.

The heteroarylene group may be a 5- or 6-membered monocyclic or fused-cyclic group containing a nitrogen atom, an oxygen atom, a sulfur atom or the like as heteroatoms. Specific examples of the heteroarylene group include a pyridinediyl group, a furandiyl group, a thiophenediyl group, a quinolinediyl group, a benzofurandiyl group, a benzothiophenediyl group, and the like. These heteroarylene groups may be substituted with substituents, and the substituents include an alkyl group, an alkoxy group, an alkylenedioxy group, a halogen atom and the like, such as those mentioned above.

As the ring formed by any two groups selected from $R^2$, $R^3$, $R^4$, $R^5$ and $R^6$ in the compound of formula (2), there may be mentioned combinations of $R^2$ and $R^3$, $R^2$ and $R^4$, $R^2$ and $R^5$, $R^2$ and $R^6$, $R^3$ and $R^4$, $R^3$ and $R^5$, $R^3$ and $R^6$, $R^4$ and $R^5$, $R^4$ and $R^6$ or $R^5$ and $R^6$. The ring is formed may be a 5- to 20-membered ring which may contain one or two heteroatoms such as an oxygen atom or a nitrogen atom, as constituent atoms of the ring. Preferred examples of the ring that is formed include monocyclic rings such as a cyclopentane ring, a cyclohexane ring, a cycloheptane ring, a cyclooctane ring, a cyclodecane ring, a cyclododecane ring, a cyclotetradecane ring, a cyclopentadecane ring, a cyclohexadecane ring and a cycloheptadecane ring; and fused rings such as a dihydronaphthalene ring, an indene ring, a dihydroquinoline ring and a dihydroisoquinoline ring. These rings may be substituted with a hydrocarbon group, a heterocyclic group, an alkoxy group or the like. Specific examples of the respective substituents include groups such as those mentioned above.

The alcohol in the mixture of an alcohol and an amine that is used in the process of the present invention is not particularly limited, but there may be mentioned an alcohol represented by the following formula (3).

$$R^7OH \quad\quad\quad (3)$$

wherein $R^7$ represents a hydrocarbon group which may be substituted, an alkoxy group which may be substituted, or a heterocyclic group which may be substituted.

Examples of the hydrocarbon group which may be substituted, the alkoxy group which may be substituted or the heterocyclic group which may be substituted, which is represented by $R^7$ in the alcohol represented in the formula (3), include the same groups as those described for the compound represented by the formula (2)

The amine in the mixture of an alcohol and an amine that is used in the production process of the present invention is not particularly limited, but there may be mentioned an amine represented by the following formula (4).

$$R^8R^9NH \quad\quad\quad (4)$$

wherein $R^8$ and $R^9$ each independently represent a hydrogen atom, a hydrocarbon group or a heterocyclic group; and $R^8$ and $R^9$ may form a ring.

The hydrocarbon group represented by $R^8$ or $R^9$ in the amine represented by the formula (4) is not particularly limited, but examples thereof include an alkyl group, a cycloalkyl group, an alkenyl group, an alkynyl group, an aryl group, and the like. Specific groups include the same groups as those described for $R^7$ of the formula (3).

As the ring that is formed by $R^8$ and $R^9$ in the compound represented by the formula (4), there may be mentioned a 4- to 8-membered saturated or unsaturated ring containing the nitrogen to which $R^8$ and $R^9$ are bonded. These rings may contain heteroatoms such as an oxygen atom and a sulfur atom. Specific examples of the ring are not intended to be limited to these, but include an azetidine ring, a pyrrolidine ring, a piperidine ring, an azepine ring, a morpholine ring, an indole ring, an isoindole ring, a carbazole ring, and the like.

Next, the carboxylic acid ester compound which is used as an acylating agent in the production process of the present invention, will be explained.

Examples of the ester compound as an acylating agent used in the present invention include aliphatic carboxylic acid esters, aromatic carboxylic acid esters, and the like. These ester compounds may be substituted with substituents that do not exert adverse effects to the production process of the present invention.

Examples of the ester compound used as an acylating agent in the present invention include alkyl esters having linear, branched or cyclic alkyl groups with 1 to 30 carbon atoms, preferably 1 to 20 carbon atoms, and more preferably 1 to 10 carbon atoms, and more preferably 1 to 5 carbon atoms, such as methyl esters, ethyl esters, propyl esters, butyl esters, hexyl esters or octyl ester; aryl esters formed from monocyclic, polycyclic or fused-cyclic aryl groups having 6 to 40 carbon atoms, preferably 6 to 30 carbon atoms, and more preferably 6 to 20 carbon atoms, and more preferably 6 to 12 carbon atoms, such as phenyl esters, biphenyl esters or naphthyl esters; aralkyl esters formed from aralkyl groups having 7 to 40, preferably 7 to 20 carbon atoms, and more preferably 7 to carbon atoms, such as benzyl esters or 1-phenethyl esters; and the like, of aliphatic carboxylic acids or aromatic carboxylic acids that will be shown below.

Preferred esters include alkyl esters having 1 to 5 carbon atoms such as methyl esters and ethyl esters.

The carboxylic acid radical of the ester compound that is used as an acylating agent in the process of the present invention may be a mono- or polycarboxylic acid having 2 to 30 carbon atoms, preferably 2 to 20 carbon atoms, and more preferably 2 to 15 carbon atoms, which may be substituted.

The aliphatic group in the aliphatic carboxylic acid ester may be a chain-like group or a cyclic group, and may be saturated or unsaturated. The aliphatic carboxylic acid may be a monocarboxylic acid, a dicarboxylic acid or a tricarboxylic acid. Specific examples of the monocarboxylic acid include acetic acid, propionic acid, butyric acid, isobutyric acid, valeric acid, isovaleric acid, hexanoic acid, cyclopentanecarboxylic acid, cyclohexanecarboxylic acid, acrylic acid, methacrylic acid, and the like. Specific examples of the dicarboxylic acid include oxalic acid, malonic acid, succinic acid, glutaric acid, adipic acid, dimethylmalonic acid, 1,1-cyclohexanedicarboxylic acid, and the like.

The aromatic group in the aromatic carboxylic acid ester may be a monocyclic, polycyclic or fused-cyclic aryl group having 6 to 36 carbon atoms, and preferably 6 to 18 carbon atoms or 6 to 12 carbon atoms; or a monocyclic, polycyclic or fused-cyclic heteroaryl group having a 3- to 8-membered, preferably 5- to 8-membered, ring containing 1 to 4, heteroatoms preferably 1 to 3 heteroatoms, and more preferably 1 to 2 heteroatoms consisting of a nitrogen atom, an oxygen atom or a sulfur atom. Specific examples of the aromatic carboxylic acid include benzoic acid, naphthalenecarboxylic acid, pyridinecarboxylic acid, quinolinecarboxylic acid, furancarboxylic acid, thiophenecarboxylic acid, terephthalic acid, isophthalic acid, naphthalenedicarboxylic acid, 1,1'-biphenyl-2,2'-dicarboxylic acid, 1,1'-binaphthalene-2,2'-dicarboxylic acid, benzenetricarboxylic acid, pyromellitic acid, and the like.

These carboxylic acids may be substituted with substituents, and the substituents include an alkyl group, an alkoxy group, a halogen atom (fluorine, chlorine, bromine, iodine), and the like.

The alkyl group as a substituent of the carboxylic acids may be a linear, branched or cyclic alkyl group, and examples thereof include a methyl group, an ethyl group, an n-propyl group, an isopropyl group, an n-butyl group, an isobutyl group, an s-butyl group, a t-butyl group, an n-pentyl group, an n-hexyl group, an n-octyl group, a cyclopropyl group, a cyclopentyl group, a cyclohexyl group, and the like.

Examples of the alkoxy group as a substituent of the carboxylic acids include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-octyloxy group, a cyclopentyloxy group, a cyclohexyloxy group, and the like.

Preferred carboxylic acid ester compounds are not particularly limited, but examples thereof include monocarboxylic acid esters such as methyl esters or ethyl esters of acetic acid, propioinic acid, butyric acid, isobutyric acid, valeric acid, isovaleric acid, hexanoic acid, cyclopentanecarboxylic acid, cyclohexanecarboxylic acid, acrylic acid, methacrylic acid, benzoic acid, 4-chlorobenzoic acid, 4-bromobenzoic acid, 4-nitrobenzoic acid, 4-cyanobenzoic acid, 4-methylbenzoic acid, 4-tetrahydropyranylbenzoic acid, 3-(5-t-butyl-4,5-dihydrooxazolin-2-yl)benzoic acid, cinnamic acid, 2-biphenylcarboxylic acid, 3-phenylpropionic acid, pyridine-2-carboxylic acid, 2-(diphenylphosphino)benzoic acid, and the like; dicarboxylic acid diesters such as dimethyl esters or diethyl esters of oxalic acid, malonic acid, succinic acid, glutaric acid, adipic acid, dimethylmalonic acid, 1,1-cyclohexanedicarboxylic acid, phthalic acid, isophthalic acid, terephthalic acid, 1,1'-biphenyl-2,2'-dicarboxylic acid, 1,1'-binaphthalene-2,2'-dicarboxylic acid, 2,6-pyridinedicarboxylic acid, 2-hydroxyisophthalic acid, and the like; and tricarboxylic acid esters such as a trimethyl ester or a diethyl ester of pyromellitic acid.

In regard to the alcohols, amines, aminoalcohols and carboxylic acid ester compounds that are used as raw materials in the production process of the present invention, commercially available compounds can be used, or can also be produced by known processes.

In the production process of the present invention, a zinc compound, preferably a zinc compound represented by the formula (1), can function as a catalyst.

The zinc compound that is used in the production process of the present invention is not particularly limited, but examples thereof include organic acid zinc salts such as zinc acetate, zinc trifluoroacetate, zinc acetoacetate and zinc acetylacetonate; sulfonic acid zinc salts such as zinc trifluoromethanesulfonate and zinc p-toluenesulfonate; inorganic zinc compounds such as zinc chloride, zinc bromide, zinc nitrate and zinc oxide; and the like. Among these, zinc trifluoroacetate is preferred. Furthermore, when hydrates for these zinc compounds exist, these hydrates can also be used in the production process of the present invention.

In the production process of the present invention, a zinc polynuclear cluster which is obtainable by heating an organic acid zinc salt, can also be used as a preferable zinc compound. The zinc polynuclear cluster used in the present invention may be a compound represented by the formula (1), in which a is 4, b is 6 and c is 1. Examples of the alkyl group, aryl group and heterocyclic group for $R^1$ of the formula (1) include those mentioned previously, and examples of substituents thereof also include those mentioned previously. Preferred $R^1$ may be an alkyl group or aryl group which may be substituted with a halogen atom or the like, and specific examples thereof include a methyl group, an ethyl group, a trifluoromethyl group, a phenyl group and the like. Specific examples of the zinc polynuclear cluster are not particularly limited, but for example, compounds such as $Zn_4(OAc)_6O$, $Zn_4(OCOEt)_6O$, $Zn_4(OPv)_6O$, $Zn_4\{OCO(CH_2)_{16}CH_3\}_6O$, $Zn_4(OCOPh)_6O$ and $Zn_4(OCOCF_3)_6O$ may be listed as preferable examples, while $Zn_4(OCOCF_3)_6O$ is particularly preferred. In the formulas exemplified, Ac represents an acetyl group, Et represents an ethyl group, Pv represents a pivaloyl group, and Ph represents a phenyl group.

The zinc polynuclear cluster represented by the formula (1), which is used in the present invention, can be obtained by processes described in known documents, for example, a process described in Chem. Commun., 2006, 2711-2713, and specifically by heating a carboxylic acid zinc salt such as zinc trifluoroacetate, or the like.

The metal compounds used in the production process of the present invention as described above, including the zinc polynuclear cluster, can be used singly or as mixtures of two or more kinds, or can also be used in combination with other zinc compounds.

In the process for producing an ester compound of the present invention, the amount of use of the zinc compound discussed above is not particularly limited, but usually a proportion of about 0.001 to 0.5 moles of zinc atoms is preferred, and a proportion of about 0.01 to 0.3 moles of zinc atoms is more preferred, with respect to 1 mole of the carboxylic acid ester compound that is used as an acylating agent.

When unsaturated alcohols, unsaturated carboxylic acid ester compounds and the like are used as raw materials in the present invention, use can be made of a polymerization inhibitor which suppresses a polymerization reaction arising from unsaturated bonds. The polymerization inhibitor is not particularly limited as long as it is a known agent, and examples thereof include phenothiazine, benzoquinone, hydroquinone, naphthoquinone, catechol, t-butylcatechol, phenol, t-butylphenol, dimethyl-t-butylphenol, cresol, t-butylcresol, and the like.

In the process for producing an ester compound of the present invention, the proportions of se of the alcohol and amine, which are raw materials, and of the carboxylic acid ester compound which is an acylating agent, are not particularly limited.

When aminoalcohols and mixtures of alcohols and amines are subjected to acylation in a hydroxyl group-selective manner, the carboxylic acid ester compound as an acylating agent is used in an amount of usually about 0.5 to 20 moles, preferably about 0.7 to 10 moles, about 0.8 to 3.0 moles, and more preferably 0.8 to 1.0 mole, with respect to 1 mole of the alcohol. When plural hydroxyl groups or aminoalcohols are subjected to a plurality of acylation reactions, it is definitely advantageous to increase the amount of use of the carboxylic acid ester compound as compared with the case described above.

The production process of the present invention is preferably carried out in a solvent, and a single solvent may be used, or plural solvents may be mixed and used. Specific examples of the solvent are not particularly limited, but they include, for example, aromatic solvents such as toluene, xylene and benzene chloride; aliphatic hydrocarbon-based solvents such as hexane, heptane and octane; ether-based solvents such as diethyl ether, diisopropyl ether, tert-butyl methyl ether, tetrahydrofuran and 1,4-dioxane; amide-based solvents such as dimethylformamide (DMF), dimethylacetamide (DMAc) and N-methylpyrrolidone (NMP); dimethyl sulfoxide (DMSO), and the like. Among these, aromatic solvents and ether-based solvents are preferred.

The production process of the present invention can be carried out in the atmosphere, but can also be carried out in an inert gas atmosphere such as nitrogen gas or argon gas. The reaction time is not particularly limited, but is usually about 1 to 45 hours, and preferably about 6 to 24 hours. The reaction temperature is not particularly limited, but the reaction is usually carried out at room temperature to about 150° C., preferably at 50 to 150° C., and more preferably at about 60 to 130° C. However, these conditions may be appropriately altered depending on the type and amount of the raw material used or the like.

After the reaction of the production process of the present invention, the intended ester compound can be obtained by carrying out post-treatments that are usually used (for example, concentration, chromatography, crystallization, or the like). Furthermore, it is needless to say that when the raw material alcohol is a racemic compound or an optically active compound, an ester compound which is racemic or optically active correspondingly to the raw material, is obtained.

EXAMPLES

The present invention will be described below in detail by way of Examples, but the present invention is not intended to be limited to these Examples by any means.

The instruments used in the analysis of compounds in the respective Examples are as described below.

$^1$H NMR (300 MHz): Varian MERCURY 300

Melting point (mp): Yanaco micro melting point apparatus

Gas chromatography (GC): Shimadzu Gas Chromatograph GC-14A

The respective yields of the compounds are yields obtained by isolation by silica gel column chromatography in Examples 1 to 24, 29 and 30. In the other Examples, the yields were quantified by gas chromatography (GC) using an internal standard substance.

Example 1

Selective Acylation of 6-aminohexan-1-ol

In an argon atmosphere, a mixture of methyl benzoate (3.0 mmol), 6-aminohexan-1-ol (3.6 mmol), $Zn_4(OCOCF_3)_6O$ (1.25 mol % in terms of the mole number of zinc atoms; in the following Examples, the amount will be similarly expressed in terms of the mole number of zinc atoms) and diisopropyl ether (5.0 ml) was heated to reflux for 18 hours, and as a result, 6-aminohexyl benzoate having an acylated hydroxyl group was obtained at a yield of 82% (the yield is based on the carboxylic acid ester. The same applies in the following). The yield of 6-benzoylaminohexyl benzoate in which an amino group and a hydroxyl group were both acylated, was 18%.

6-Aminohexyl benzoate

Pale Yellow Oil:

$^1$H-NMR ($CDCl_3$, 35° C.) δ 1.4-1.5 (m, 4H, methylene), 1.59 (tt, J=7.5, 6.9 Hz, 2H, methylene), 1.77 (tt, J=7.5, 6.9 Hz, 2H, methylene), 2.81 (t, J=7.5 Hz, 2H, $NHCH_2$), 3.90 (bs, 2H, $NH_2$), 4.30 (t, J=6.6 Hz, 2H, $OCH_2$), 7.4-7.6 (m, 3H, Ph), 8.0-8.1 (m, 2H, Ph)

Example 2

Selective Acylation of 8-aminooctan-1-ol

In an argon atmosphere, a mixture of methyl benzoate (3.0 mmol), 8-aminooctan-1-ol (3.6 mmol), $Zn_4(OCOCF_3)_6O$ (1.25 mol % in terms of mole number) and diisopropyl ether (5.0 ml) was heated to reflux for 20 hours, and as a result, 8-aminooctyl benzoate was obtained at a yield of 90%. The yield of 8-benzoylaminooctyl benzoate was 7%.

8-Aminooctyl benzoate

Pale yellow crystal: m.p. 60-62° C.
$^1$H-NMR (CDCl$_3$, 35° C.) δ 1.3-1.5 (m, 10H, methylene), 1.76 (tt, J=6.9, 6.9 Hz, 2H, OCH$_2$CH$_2$), 2.10 (bs, 2H, NH$_2$), 2.68 (t, J=6.9 Hz, 2H, NH$_2$CH$_2$), 4.31 (t, J=6.9 Hz, 2H, OCH$_2$), 7.4-7.6 (m, 3H, Ph), 8.0-8.1 (m, 2H, Ph)

Example 3

Selective Acylation of 10-aminodecan-1-ol

In an argon atmosphere, a mixture of methyl benzoate (3.0 mmol), 10-aminodecan-1-ol (3.6 mmol), $Zn_4(OCOCF_3)_6O$ (1.25 mol % in terms of mole number) and diisopropyl ether (5.0 ml) was heated to reflux for 20 hours, and as a result, 10-aminodecyl benzoate was obtained at a yield of 90%. The yield of 10-benzoylaminodecyl benzoate was 7%.

10-Aminodecyl benzoate

Pale yellow crystal: m.p. 68-70° C.
$^1$H-NMR (CDCl$_3$, 35° C.) δ 1.3-1.5 (m, 16H, methylene, NH$_2$), 1.76 (tt, J=6.6, 6.6 Hz, 2H, OCH$_2$CH$_2$), 2.67 (t, J=6.6 Hz, 2H, NH$_2$CH$_2$), 4.31 (t, J=6.6 Hz, 2H, OCH$_2$), 7.4-7.5 (m, 3H, Ph), 8.0-8.1 (m, 2H, Ph)

Example 4

Selective Acylation of 6-aminohexan-2-ol

In an argon atmosphere, a mixture of methyl benzoate (1.0 mmol), 6-aminohexan-2-ol (1.2 mmol), $Zn_4(OCOCF_3)_6O$ (1.25 mol % in terms of mole number) and toluene (1.7 ml) was heated to reflux for 46 hours, and as a result, 6-amino-2-hexyl benzoate was obtained at a yield of 66%. The yield of 6-benzoylamino-2-hexyl benzoate was 21%.

6-Amino-2-hexyl benzoate

Oil:
$^1$H-NMR (CDCl$_3$, 35° C.) δ 1.34 (d, J=6.3 Hz, 3H, CH$_3$), 1.4-1.8 (m, 6H, methylene), 2.10 (bs, 3H, OH, NH$_2$), 2.69 (t, J=6.9 Hz, 2H, NH$_2$CH$_2$) 5.16 (qt, J=6.3, 6.3 Hz, 1H, OCH), 7.3-7.6 (m, 3H, Ph), 8.0-8.1 (m, 2H, Ph)

Example 5

Selective Acylation of [(4-aminomethyl)phenyl]methanol

In an argon atmosphere, a mixture of methyl benzoate (3.0 mmol), [(4-aminomethyl)phenyl]methanol (3.6 mmol), $Zn_4(OCOCF_3)_6O$ (1.25 mol % in terms of mole number) and diisopropyl ether (5.0 ml) was heated to reflux for 18 hours, and as a result, [(4-aminomethyl)phenyl]methyl benzoate was obtained at a yield of 55%. The yields of N-[(4-hydroxymethyl)benzyl]benzamide and [(4-benzoylaminomethyl)phenyl]methyl benzoate were 7% and 17%, respectively.

Example 6

Selective Acylation of 1-[(4-aminomethyl)phenyl]ethanol

In an argon atmosphere, a mixture of methyl benzoate (1.0 mmol), 1-[(4-aminomethyl) phenyl]ethanol (1.2 mmol), $Zn_4(OCOCF_3)_6O$ (1.25 mol % in terms of mole number) and toluene (1.7 ml) was heated to reflux for 18 hours, and as a result, 1-[4-(aminomethyl)phenyl]ethyl benzoate was obtained at a yield of 62%. The yield of [4-(benzoylaminomethyl)phenyl]ethyl benzoate was 28%.

1-[4-(Aminomethyl) phenyl]ethyl benzoate

Oil:
$^1$H-NMR (CDCl$_3$, 35° C.) 1.57 (bs, 2H, NH$_2$), 1.66 (d, J=6.6 Hz, 3H, CH$_3$), 3.83 (s, 2H, NH$_2$CH$_2$), 6.12 (q, J=6.6 Hz, 1H, OCH), 7.3-7.6 (m, 7H, Ph, Ar), 8.0-8.1 (m, 2H, Ar)

Example 7

Selective Acylatino of pyrrolidin-3-ol

In an argon atmosphere, a mixture of methyl benzoate (3.0 mmol), pyrrolidin-3-ol (3.6 mmol), $Zn_4(OCOCF_3)_6O$ (1.25 mol % in terms of mole number) and diisopropyl ether/1,4-dioxane (3/1) (5.0 ml) was heated to reflux for 46 hours, and as a result, pyrrolidin-3-yl benzoate was obtained at a yield of 66%. The yield of N-benzoylpyrrolidin-3-yl benzoate was 34%.

Example 8

Selective Acylation of piperidin-4-ol

In an argon atmosphere, a mixture of methyl benzoate (3.0 mmol), piperidin-4-ol (3.6 mmol), $Zn_4(OCOCF_3)_6O$ (1.25 mol % in terms of mole number) and diisopropyl ether/1,4-dioxane (3/1) (5.0 ml) was heated to reflux for 46 hours, and as a result, piperidin-4-yl benzoate was obtained at a yield of 65%. The yield of N-benzoylpiperidin-4-yl benzoate was 30%.

Example 9

Selective Acylation of piperidin-4-ylmethanol

In an argon atmosphere, a mixture of methyl benzoate (1.0 mmol), piperidin-4-ylmethanol (1.2 mmol), $Zn_4(OCOCF_2)_6O$ (1.25 mol % in terms of mole number) and toluene (1.7 ml) was heated to reflux for 18 hours, and as a result, piperidin-4-ylmethyl benzoate was obtained at a yield of 88%. The yield of N-benzoylpiperidin-4-ylmethyl benzoate was 12%.

Piperidin-4-ylmethyl benzoate

Yellow Oil:
$^1$H-NMR (CDCl$_3$, 35° C.) δ 1.33 (ddd, J=12.6, 12.0, 4.2 Hz, 2H, piperidine), 1.80 (d, J=12.6 Hz, 2H, piperidine), 1.9-2.0 (m, 1H, piperidine), 2.43 (bs, 1H, NH), 2.65 (ddd, J=12.0, 12.0, 2.4 Hz, 2H, piperidine), 3.13 (d, J=12.0 Hz, 2H, piperidine), 4.18 (d, J=6.6 Hz, 2H, OCH$_2$), 7.4-7.6 (m, 3H, Ph), 8.0-8.1 (m, 2H, Ph)

Example 10

Selective Acylation of 2-(piperidin-4-yl)ethanol

In an argon atmosphere, a mixture of methyl benzoate (1.0 mmol), 2-(piperidin-4-yl)ethanol (1.2 mmol), Zn$_4$(OCOCF$_2$)$_6$ O (1.25 mol % in terms of mole number) and toluene (1.7 ml) was heated to reflux for 18 hours, and as a result, 2-(piperidin-4-yl) ethyl benzoate was obtained at a yield of 92%. The yield of 2-(N-benzoylpiperidin-4-yl)ethyl benzoate was 7%.

2-(Piperidin-4-yl) ethyl benzoate

Yellow Oil:
$^1$H-NMR (CDCl$_2$, 35° C.) δ 1.22 (ddd, J=24.0, 12.0, 3.9 Hz, 2H, piperidine) 1.5-1.7 (m, 1H, piperidine), 1.73 (td, J=6.6, 6.6 Hz, 2H, OCH$_2$CH$_2$) 1.7-1.8 (m, 2H, piperidine) 2.62 (ddd, J=12.0, 12.0, 2.4 Hz, 2H, piperidine) 2.5 (bs, 1H, NH), 3.10 (d, J=12.0 Hz, 2H, piperidine) 4.37 (t, J=6.6 Hz, 2H, OCH$_2$), 7.4-7.6 (m, 3H, Ph), 8.0-8.1 (m, 2H, Ph)

Example 11

Selective Acylation of trans-4-aminocyclohexan-1-ol

In an argon atmosphere, a mixture of methyl benzoate (1.0 mmol), trans-4-aminocyclohexan-1-ol (1.2 mmol), Zn$_4$(OCOCF$_3$)$_6$O (1.25 mol % in terms of mole number) and toluene (1.7 ml) was heated to reflux for 24 hours, and as a result, trans-4-aminocyclohexyl benzoate was obtained at a yield of 99%.

Trans-4-aminocyclohexyl benzoate

Pale Yellow Oil:
$^1$H-NMR (CDCl$_2$, 35° C.) δ 1.29 (dddd, J=12.9, 12.9, 10.5, 3.6 Hz, 2H, α-cyclohexyl), 1.38 (bs, 2H, NH$_2$), 1.56 (dddd, J=12.9, 12.9, 10.5, 3.9 Hz, 2H, α-cyclohexyl), 1.9-2.0 (m, 2H, eq-cyclohexyl), 2.1-2.2 (m, 2H, eq-cyclohexyl), 2.78 (tt, J=10.5, 3.9 Hz, 1H, NCH), 4.94 (tt, J=10.5, 3.9 Hz, 1H, OCH), 7.4-7.6 (m, 3H, P h), 8.0-8.1 (m, 2H, Ph)

Example 12

Selective Esterification in Mixture of Cyclohexanol and Cyclohexylamine

In an argon atmosphere, a mixture of methyl benzoate (1.0 mmol), cyclohexanol (1.2 mmol), cyclohexylamine (1.2 mmol), Zn$_4$(OCOCF$_3$)$_6$O (1.25 mol in terms of mole number) and diisopropyl ether (1.7 ml) was heated to reflux for 18 hours. The yield of cyclohexyl benzoate was 96%. The yield of cyclohexylbenzamide was 1%.

Examples 13 to 24

Selective Esterification in Mixture of Cyclohexanol and Cyclohexylamine

Reactions were carried out in the same manner as in Example 12 using various acylating agents, and the results are summarized and presented in the following Table 1.

TABLE 1

| Example | Substrate | | Acylating agent | Reaction time (hr) |
| --- | --- | --- | --- | --- |
| | Alcohol | Amine | ester | |
| 13 | cyclohexanol-OH | cyclohexyl-NH$_2$ | MeO-C(=O)-(CH$_2$)$_9$-OTBS | 24 |
| 14 | cyclohexanol-OH | cyclohexyl-NH$_2$ | MeO-C(=O)-C$_6$H$_4$-Me | 24 |
| 15 | cyclohexanol-OH | cyclohexyl-NH$_2$ | MeO-C(=O)-C$_6$H$_4$-Cl | 24 |
| 16 | cyclohexanol-OH | cyclohexyl-NH$_2$ | MeO-C(=O)-C$_6$H$_4$-Br | 24 |

TABLE 1-continued

| Example | Alcohol | Amine | Ester | Time (h) |
|---|---|---|---|---|
| 17 | cyclohexanol-OH | cyclohexyl-NH₂ | MeO-C(O)-C₆H₄-NO₂ (para) | 18 |
| 18 | cyclohexanol-OH | cyclohexyl-NH₂ | MeO-C(O)-C₆H₄-CN (para) | 18 |
| 19 | cyclohexanol-OH | cyclohexyl-NH₂ | MeO-C(O)-C₆H₄-OTHP (para) | 24 |
| 20 | cyclohexanol-OH | cyclohexyl-NH₂ | MeO-C(O)-C₆H₄-Br (meta) | 18 |
| 21 | cyclohexanol-OH | cyclohexyl-NH₂ | MeO-C(O)-C₆H₄-(4,5-dihydrooxazol-2-yl with 4-t-Bu) (meta) | 18 |
| 22 | cyclohexanol-OH | cyclohexyl-NH₂ | MeO-C(O)-CH=CH-Ph (trans) | 18 |
| 23 | cyclohexanol-OH | cyclohexyl-NH₂ | MeO-C(O)-CH₂CH₂-Ph | 18 |
| 24 | cyclohexanol-OH | cyclohexyl-NH₂ | Me-C(O)-(CH₂)₁₆-Me | 18 |

| | Product | |
|---|---|---|
| Example | Ester compound | Amide compound |
| 13 | Cyclohexyl-OCO(CH₂)₉OTBS — 87% | Cyclohexyl-NHCO(CH₂)₉OTBS — ND |
| 14 | Cyclohexyl ester of 4-methylbenzoic acid — >99% | Cyclohexyl amide of 4-methylbenzoic acid — ND |

TABLE 1-continued
| | | |
|---|---|---|
| 15 | 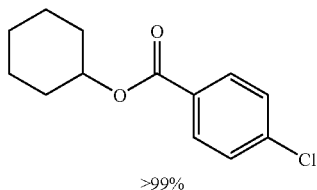 >99% | 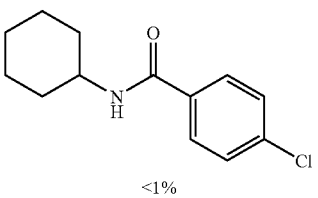 <1% |
| 16 | 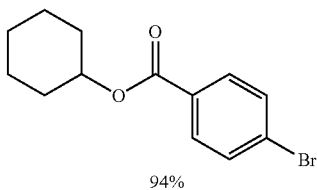 94% | 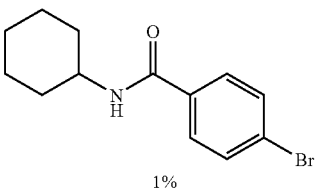 1% |
| 17 | 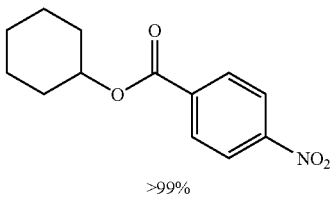 >99% | 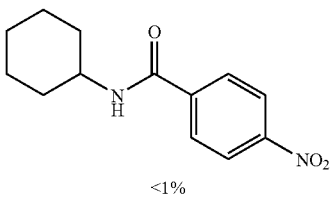 <1% |
| 18 | 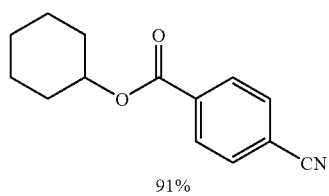 91% | 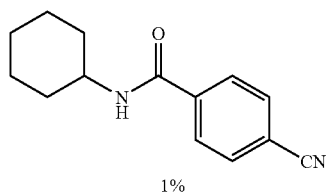 1% |
| 19 | 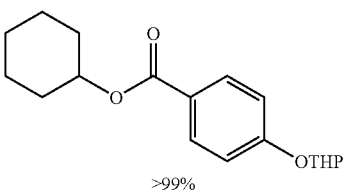 >99% | 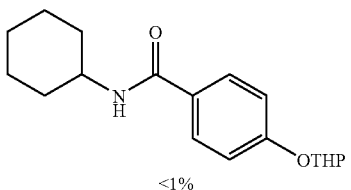 <1% |
| 20 | 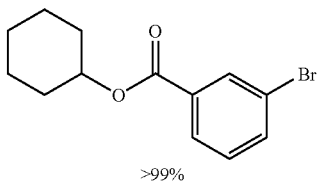 >99% | 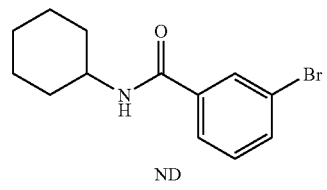 ND |
| 21 | 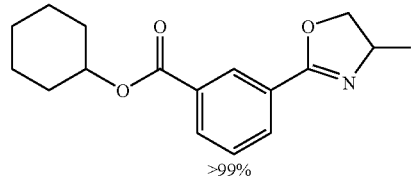 >99% | 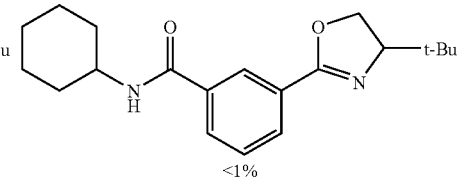 <1% |
| 22 | 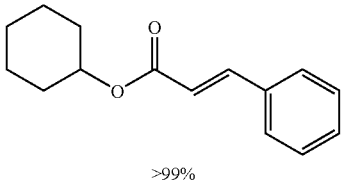 >99% | 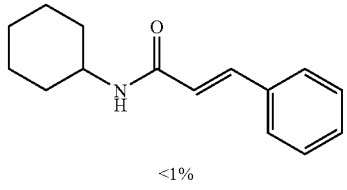 <1% |

TABLE 1-continued

| | | | |
|---|---|---|---|
| 23 | cyclohexyl 3-phenylpropanoate, 94% | N-cyclohexyl 3-phenylpropanamide, <1% | |
| 24 | cyclohexyl OCO(CH₂)₁₆CH₃, 98% | cyclohexyl NHCO(CH₂)₁₆CH₃, 8% | |

Example 25

Selective Acylation in Mixture of Alcohol and Amine, Using Methyl Benzoate

In an argon atmosphere, a mixture of methyl benzoate (1.0 mmol), 1-hexanol (1.2 mmol), 1-hexylamine (1.2 mmol), $Zn_4(OCOCF_3)_6O$ (1.25 mol % in terms of mole number) and diisopropyl ether (1.7 ml) was heated to reflux for 18 hours. The resulting reaction solution was quantified by GC, and the yield of 1-hexyl benzoate was 92%. The yield of 1-hexylbenzamide was 8%.

Examples 26 to 35

Selective Acylation in Mixture of Alcohol and Amine, Using Methyl Benzoate

Reactions were carried out in the same manner as in Example 25 using various alcohols and amines, and the results are summarized and presented in the following Table 2.

TABLE 2

| Example | Substrate | | Acylating agent |
|---|---|---|---|
| | Alcohol | Amine | ester |
| 26 | 1-phenylethanol | 1-phenylethylamine | methyl benzoate |
| 27 | 4-heptanol | 4-heptylamine | methyl benzoate |
| 28 | neopentyl alcohol | neopentylamine | methyl benzoate |
| 29 | 1-indanol | 1-aminoindane | methyl benzoate |
| 30 | 1,2,3,4-tetrahydro-1-naphthol | 1,2,3,4-tetrahydro-1-naphthylamine | methyl benzoate |

TABLE 2-continued

| | Alcohol | Amine | Ester reagent |
|---|---|---|---|
| 31 | cyclohexanol | pyrrolidine | methyl benzoate |
| 32 | cyclohexanol | piperidine | methyl benzoate |
| 33 | cyclohexanol | morpholine | methyl benzoate |
| 34 | 1-hexanol | cyclohexylamine | methyl benzoate |
| 35 | cyclohexanol | hexylamine | methyl benzoate |

| | Product | |
|---|---|---|
| Example | Ester compound | Amide compound |
| 26 | PhC(O)O-CH(CH₃)-Ph, 76% | PhC(O)NH-CH(CH₃)-Ph, <1% |
| 27 | 4-(OCOPh)heptane, 90% | 4-(NHCOPh)heptane, 1% |
| 28 | neopentyl benzoate, 94% | neopentyl benzamide, 1% |
| 29 | 1-indanyl benzoate, 95% | 1-indanyl benzamide, ND |
| 30 | 1-tetralinyl benzoate, 78% | 1-tetralinyl benzamide, ND |

Example 36

Selective Acylation of piperidin-4-ylmethanol

In an argon atmosphere, a mixture of ethyl acetate (51.2 mmol), piperidin-4-ylmethanol (3.0 mmol) and $Zn_4(OCOCF_3)_6O$ (1.25 mol % in terms of mole number) was heated to reflux for 18 hours, and as a result, piperidin-4-ylmethyl benzoate was obtained as a single product at a yield of 97%.

Example 37

Selective Esterification in Mixture of Cyclohexanol and Cyclohexylamine

In an argon atmosphere, a mixture of ethyl acetate (1.7 mL, 0.6 M), cyclohexanol (1.0 mmol), cyclohexylamine (1.0 mmol) and $Zn_4(OCOCF_3)_6O$ (1.25 mol % in terms of mole number) was heated to reflux for 18 hours. The yield of cyclohexyl acetate was 89%. The yield of cyclohexylacetamide was 6%.

INDUSTRIAL APPLICABILITY

The present invention provides a process for selectively acylating an alcoholic hydroxyl group in a reaction system in which a nucleophilic functional group such as an amino group is present. More particularly, the present invention provides a process which is capable of carrying out selective acylation of an alcoholic hydroxyl group in aminoalcohols under mild reaction conditions, with good sustainability, operability and economic efficiency, and provides a process that is very useful in the fields of synthetic chemistry such as medicine and agrochemicals.

The invention claimed is:

1. A process for producing an ester compound comprising reacting an aminoalcohol represented by general formula (2):

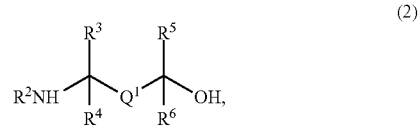

wherein
R² represents a hydrogen atom, a hydrocarbon group which may be substituted, or an alkoxycarbonyl group which may be substituted;
R³, R⁴, R⁵ and R⁶, which may be identical or different, and each represent a hydrogen atom, a hydrocarbon group which may be substituted, an alkoxy group which may be substituted, or a heterocyclic group which may be substituted, or any two groups selected from R², R³, R⁴, R⁵ and R⁶ may be joined to form a ring; and
Q¹ represents a linking group selected from the group consisting of an alkylene group, an arylene group and a heteroarylene group,
with a carboxylic acid ester compound in the presence of a compound containing a zinc element, thereby selectively acylating a hydroxyl group of the aminoalcohol.

2. The process for producing an ester compound according to claim 1, wherein the compound containing the zinc element is a compound represented by formula (1):

wherein
R1 represents an alkyl group which may be substituted, an aryl group which may be substituted, or a heterocyclic group which may be substituted;

Z represents an oxygen atom, a sulfur atom or a selenium atom;

a represents 1 or 4, b represents 2 or 6, and c represents 0 or 1, provided that when a=1, b=2 and c=0, and when a=4, b=6 and c=1.

* * * * *